United States Patent
Lewis

(10) Patent No.: US 9,675,572 B2
(45) Date of Patent: Jun. 13, 2017

(54) INTRAVENOUS OMEGA-3 FATTY ACID COMPOSITIONS AND METHOD OF USE

(75) Inventor: Michael Lewis, Rockville, MD (US)

(73) Assignee: THE UNITED STATES OF AMERICA AS REPRESENTED BY THE SECRETARY OF THE ARMY, Washington, DC (US)

( * ) Notice: Subject to any disclaimer, the term of this patent is extended or adjusted under 35 U.S.C. 154(b) by 173 days.

(21) Appl. No.: 13/637,239

(22) PCT Filed: Apr. 22, 2011

(86) PCT No.: PCT/US2011/033542
§ 371 (c)(1),
(2), (4) Date: Jan. 28, 2013

(87) PCT Pub. No.: WO2011/133841
PCT Pub. Date: Oct. 27, 2011

(65) Prior Publication Data
US 2013/0137770 A1    May 30, 2013

Related U.S. Application Data

(60) Provisional application No. 61/327,252, filed on Apr. 23, 2010.

(51) Int. Cl.
| | |
|---|---|
| *A61K 31/202* | (2006.01) |
| *A61K 9/00* | (2006.01) |
| *A61K 31/201* | (2006.01) |
| *A61K 47/14* | (2006.01) |
| *A61K 9/107* | (2006.01) |

(52) U.S. Cl.
CPC .......... *A61K 31/202* (2013.01); *A61K 9/0019* (2013.01); *A61K 9/107* (2013.01); *A61K 31/201* (2013.01); *A61K 47/14* (2013.01)

(58) Field of Classification Search
None
See application file for complete search history.

(56) References Cited

U.S. PATENT DOCUMENTS 5,874,470 A * 2/1999 Nehne ............... A61K 31/20
514/458

FOREIGN PATENT DOCUMENTS

| CA | 2511902 A1 | 7/2003 |
|---|---|---|
| EP | 0 863 754 | 12/2009 |
| WO | 90/08544 A1 | 8/1990 |
| WO | 01/89474 A2 | 11/2001 |
| WO | 2007070307 A2 | 6/2007 |
| WO | 2008036353 A2 | 3/2008 |
| WO | 2010104575 A2 | 9/2010 |

OTHER PUBLICATIONS

Wikipedia.com "Soybean oil" (Jan. 2010).*
KIC Chemicals, Inc. "Caprylic/Capric Triglycerides (MCT Oil)" (1999).*
Belayev et al. "Docosahexaenoic acid complexed to albumin elicits highgrade ischaemic neuroprotection" Stroke 36, 118-123 (2005).*
Michael-Titus Omega-3 Fatty Acids: Their Neuroprotective and Regeneratvie Potential in Traumatic Neurological Injury, Jun. 2009.*
"prophylaxis" definition at www.dictionary.com, accessed online on Mar. 3, 2016.*
International Search Report for International Application No. PCT/US2011/033542, mailed Feb. 8, 2012.
Calder, P.C. "Long-chain n-3 fatty acids and inflammation: potential application in surgical and trauma patients." Brazilian Journal of Medical and Biological Research. 2003, vol. 36, No. 4, pp. 433-446.
Carpentier et al., "Rapid cellular enrichment of eicosapentaenoate after a single intravenous injection of a novel medium-chain triacylglycerol:fish-oil emulsion in humans", American Journal of Clinical Nutrition, vol. 91, No. 4, Feb. 10, 2010 (Feb. 10, 2010), pp. 875-882.

* cited by examiner

Primary Examiner — Carlos Azpuru
Assistant Examiner — Casey Hagopian
(74) Attorney, Agent, or Firm — McAndrews, Held & Malloy, Ltd.

(57) ABSTRACT

The invention encompasses intravenous pharmaceutical compositions containing omega-3 fatty acids and methods of treating traumatic brain injury, traumatic spinal cord injury and/or stroke using these pharmaceutical compositions.

14 Claims, No Drawings

INTRAVENOUS OMEGA-3 FATTY ACID COMPOSITIONS AND METHOD OF USE

REFERENCE TO RELATED APPLICATIONS

This application is a U.S. national stage application filed under 35 U.S.C. 371 of international application PCT/US2011/033542, filed Apr. 22, 2011, which claims the benefit of U.S. Provisional Application No. 61/327,252 filed Apr. 23, 2010, the entirety of both of which is hereby incorporated by reference.

FIELD OF THE INVENTION

This present invention relates to intravenous pharmaceutical compositions comprising at least one omega-3 essential fatty acids and methods of modulating inflammatory response in a subject undergoing traumatic brain injury, non-traumatic brain injury or spinal cord injury.

DESCRIPTION OF THE BACKGROUND

Traumatic brain injury (TBI) is the most common cause of death and acquired disability among children and young adults in developed countries. Each year in the United States there are approximately 1.6 million cases of TBI, with 300,000 patients requiring hospitalization, and 90,000 patients suffering permanent impairment. Approximately 50% of cases of severe TBI are associated with extracranial injuries; between 5 and 10% of cases with moderate or severe TBI also present with spinal cord injury at cervical level. TBI is a leading cause of combat casualties and modern warfare is associated with a significant increase in blast-induced injuries (Michael-Titus (2009) Clin Lipidology, 4: 343-353). The clinical outcome of these patients is determined not only by the primary brain lesions (laceration, contusion, shearing and axonal stretching), but also by the extent of secondary brain damage caused by the severity of the post-traumatic inflammatory response. Secondary brain damage after traumatic brain injury involves neuroinflammatory mechanisms, mainly dependent on the intracerebral production of cytokines (Chiaretti (2008) Eur. J. Paediatr. Neurol. 12:195-204).

Blast related TBI is of particular concern to the United States Department of Defense because it can lead to permanent neurological injury and deficits. Blast related TBI, often caused by Improvised Explosive Devices (IED), has inflicted significant harm to U.S. and coalition forces (Martin (2008) Am. J. Nurs. 108: 40-47; Warden (2006) J. Head Trauma Rehabil. 21: 398-402; Zeitzer (2008) AAOHN J. 56: 347-53). Even though TBI advancements in body and vehicle armor have improved survival rate from high order explosives, traumatic brain injury remains a significant clinical challenge. Blast-related, closed-head injury is the most common presentation of TBI, and the inflicted damage can result in permanent neurological dysfunction of varying degrees (cognitive and motor deficits, neuropsychiatric and post-traumatic stress disorders, etc.).

Medical treatment of TBI in the unconscious soldier is currently mainly based on emergency, life-saving clinical maneuvers performed by the far forward medical provider including volume resuscitation, protecting airway with sufficient ventilation and oxygenation, and maintenance of vital organ systems in the field of battle, then during transport to the next echelon of care, and after arrival at the higher echelon during the critical care period.

Non-traumatic brain injury such as stroke is the third leading cause of death in the United States behind only heart disease and cancer. About 137,000 Americans die of stroke every year and causes 10% of deaths worldwide. Every year, about 795,000 people in the United States have a stroke. About 610,000 of these are first or new strokes. About 185,000 people who survive a stroke go on to have another. The incidence of stroke increases exponentially from 30 years of age, and etiology varies by age. Advanced age is one of the most significant stroke risk factors. 95% of strokes occur in people age 45 and older, and two-thirds of strokes occur in those over the age of 65. Men are 25% more likely to suffer strokes than women, yet 60% of deaths from stroke occur in women. Some risk factors for stroke apply only to women. Primary among these are pregnancy, childbirth, menopause and the treatment thereof.

Likewise, spinal cord injury (SCI) affects a significant number of patients worldwide. At present, the number of survivors of SCI in the United States is around 250,000 and the annual incidence is approximately 40 cases per million. SCI occurs mainly as a consequence of road accidents, falls and acts of violence and many of the affected are young, as most injuries tend to occur between the ages of 16 and 30. The neurological impairment which follows SCI leads to a significantly reduced quality of life for the patient, and is also associated with a marked personal burden for families (Michael-Titus (2007) PLEFA 77:295-300).

SCI and TBI caused by a penetrating kinetic force (e.g., gunshot wound), mechanical force, or fall, or the blast or shock wave from high order explosives, can cause significant internal traumatic injury to the body and brain. Damage to the brain usually occurs in two stages. The primary phase of injury occurs immediately after the moment of impact causing percussion trauma to the brain tissues and nerve structures. It is often accompanied by disruptions in cerebral blood flow and the cerebrospinal fluid system and is evident in the period immediately following the injury (from minutes to a couple of hours). Vasoconstriction and ischemia occur as a result of neuro-inflammation and edema. The secondary injury is a systemic inflammatory response that accompanies head injury and is associated with chronic inflammation, oxidative stress, and likely permanent damage to individual nerve cells through neural apoptosis and necrosis. This phase continues for days or weeks following injury and can be devastating to the neurologic system or in some cases may result in death of the patient (Bauman (2009) J Neurotrauma 26: 841-860).

At present, the medical management of trauma patients, in particular those suffering a traumatic brain injury, does not include the use of effective anti-inflammatory therapy to address the systemic inflammatory response to trauma or to provide the substrate to begin the repair and rebuilding process of the brain following TBI.

Lipids are a broad group of naturally occurring molecules which includes fats, waxes, sterols, fat-soluble vitamins (such as vitamins A, D, E and K), monoglycerides, diglycerides, phospholipids, and others. Lipids generally have poor solubility in water. Lipids are classified as neutral lipids (triglycerides, steroids, and waxes) and polar lipids (phospholipids, glycolipids and lipoproteins). Triglycerides are esters of glycerol and fatty acids (FA). A fatty acid is a carboxylic acid with a long unbranched aliphatic tail (chain), which is either saturated or unsaturated. Fatty acids can be characterized by the length of the chains (2-4 carbon atoms=short-chain fatty acids, 6-12 carbon atoms=medium-chain fatty acids, 16-24 carbon atoms=long-chain fatty acids) and the number of carbon-carbon double bonds (no double bond=saturated, 1 double bond=monounsaturated, 2-3 double bonds polyunsaturated, more than 3 double bonds=highly polyunsaturated).

There are three fatty acid families commonly known as omega-3, 6, and 9 where omega characterizes the position of the first carbon-carbon double bond. The corresponding fatty acid families start with fatty acids having eighteen carbon atoms. The human body can add carbon-carbon double bonds through desaturation and create higher homologues via elongation (Bistrian (2003) JPEN 27, 168-175). All three fatty acid families use the same enzyme system for this purpose and the rate-limiting step is the desaturation by the 6-desaturase. How much of the higher and more unsaturated homologues of the fatty acid families are synthesized depends mainly on the affinity to the enzyme system and the amount supplied in the diet. The affinity of the fatty acids to the elongase-desaturase enzyme system is highest for omega-3, lower for the omega-6 and very low for the omega-9 fatty acids.

Eicosapentanenoic acid (commonly known as EPA; 20:5n-3(ω-3 or omega-3)) and docosahexaenoic acid (commonly known as DHA; 22:6 (ω-3 or omega-3)) are omega-3 essential fatty acids (omega-3 EFA) most often commercially manufactured from refinement and distillation of fish oil or produced commercially from fish oil. Most of the omega-3 fatty acids in fish and other more complex organisms originates in various photosynthetic and heterotrophic microalgae, and concentrates in organisms as it moves up the food chain. Omega-3 fatty acids are commercially manufactured from refinement and distillation of fish oils and from microalgae. DHA is the most abundant essential fatty acid (polyunsaturated fatty acids or PUFAs) in the brain and retina. It comprises 40% of the PUFA in the brain (97% of the omega-3 EFA) and 60% of the PUFA in the retina (93% of the omega-3 EFA). About 50% of the weight of the neuron's plasma membrane is composed of DHA.

While fish oil supplements are ubiquitous in the food marketplace for oral consumption and available in hospitals in the form of liquid enteric feeding (e.g., nasogastric tube or gastric peg tube feeding), there are no omega-3-based fatty acids approved by the United States Food and Drug Administration for intravenous administration or total parenteral nutrition (TPN). Soybean oil based lipid emulsions are the only parenteral nutrition products that have ever been approved in the United States (McClave (2009) J. Parenter. Enteral. Nutr. 33: 277-316) and none are adequate, suitable, or desirable for use in the trauma setting due to their richness in omega-6 fatty acids, which foster a proinflammatory state. Soybean oil is a major source of omega-6 fatty acids which predominate as precursors to arachidonic acid, the highly vasoactive, proinflammatory 2-series prostaglandins and thromboxanes along with the 4-series leukotrienes.

Presently, there are only three commercially available parenteral lipid emulsions containing fish oil derived omega-3 fatty acids in clinical use in Europe and none in the United States. The first product available on the market was Omegaven™ (Fresenius Kabi), a 10% fish oil-in-water emulsion. The second product, Lipoplus™ (B. Braun), is a physical mixture of oils of Medium chain triglycerides or MCT (50%); Soybean (40%) and Fish Oil (10%). The most recent product is SMOFlipid™ (Fresenius Kabi), and is also a physical mixture of oils: soybean oil (30%), MCT oil (30%), Olive oil (25%) and fish oil (15%). Of note, Lipoplus™ and SMOFlipid™ contain 40% and 30% soybean oil, respectively. Soybean oil however, fosters a pro-inflammatory environment. Although Omegaven™ is a pure fish oil emulsion, it has a low-quality fish oil source and the product is a 10% oil-in-water emulsion. Since the early 1960's, Omegaven™ is the only parenteral nutrition product marketed not using a 20% oil-in-water emulsion. Twenty percent oil-in-water emulsions are considered the standard in the industry. Additionally, Omegaven™ requires significantly more volume to be administered because it is half the concentration and contains half the amount of omega-3 fatty acids compared to fish oil that complies with European Pharmacopeia monograph EP1352. Furthermore, the 10% emulsion uses 1.2% (w/v) of egg phospholipids as the emulsifier, the same as found in a 20% formulation. The excess emulsifier forms separate liposomes/micelles that have been shown to interfere with lipoprotein lipase, impairing plasma clearance of lipids, and leading to hypertriglyceridemia (Driscoll (2001) In: Parenteral Nutrition, W.B. Saunders, pp. 35-59).

The present invention provides a stable omega-3 fatty acids based intravenous pharmaceutical composition that would provide a route of administration for optimum bioavailability to be used as an immediate intravenous bolus in an emergency situation (e.g., by emergency medical technicians in an ambulance on the way to a hospital emergency room following an accident, multi-trauma or head injury, on combat situations where the wounded are being transported to a treatment facility) and follow-on intravenous infusion for extended period of time to ameliorate the immediate aftermath of trauma.

SUMMARY OF THE INVENTION

The present invention provides a 20% oil-in-water intravenous pharmaceutical composition comprising omega-3 essential fatty acids. The present invention also provides a method of treatment for a patient undergoing traumatic brain injury, spinal cord injury or stroke comprising intravenous administration of a highly bioavailable, safe and stable intravenous pharmaceutical composition comprising at least one omega-3 essential fatty acid that consists of intravenous administration as soon as possible following injury, preferably within 30-120 minutes, followed by a continuous intravenous infusion for up to 21 days.

The present invention thus encompasses an intravenous pharmaceutical composition comprising an oil phase comprising at least one omega-3 essential fatty acid selected from a group consisting of α-linolenic acid (ALA), eicosapentaenoic acid (EPA), and docosahexaenoic acid (DHA), and at least one medium chain triglyceride (MCT), at least one emulsifier; and an aqueous phase, wherein the omega-3 essential fatty acid is in a concentration of about 50% to about 90% by weight of the oil phase.

In some embodiments the omega-3 essential fatty acids are EPA and DHA combined or DHA alone. The concentration range in the pharmaceutical composition of the omega-3 fatty acids can be about 50 g/L to about 300 g/L.

In some embodiments, the medium chain triglycerides are caprylic acid and capric acid. The caprylic acid and capric acid can be in a ratio range of about 3:2 by weight.

In some embodiments, the oil phase and aqueous phase are in a ratio of about 1:5 by volume. In some embodiments, the emulsifier is selected from the group consisting of egg yolk phospholipid, soy lecithin, sesame oil, safflower oil, and cottonseed oil. The egg yolk phospholipid can be in a concentration of about 1.2% (w/v).

In some embodiments, the aqueous phase of the pharmaceutical composition comprises at least one antioxidant and/or at least one osmotic agent. The osmotic agent can be glycerol and the antioxidant can be α-tocopherol.

In some embodiments, omega-6 fatty acids are absent from the pharmaceutical composition containing omega-3 fatty acids. The intravenous pharmaceutical composition can comprise about 5 to about 15 g/L of ALA and about 100 to about 125 g/L of EPA and DHA combined, about 25 g/L of glycerol; about 12 g/L of egg yolk phospholipids; and about 100 mg/L of α-tocopherol.

The invention also encompasses a method of treating a subject suffering from traumatic brain injury, spinal cord injury and/or stroke comprising intravenously administering the pharmaceutical composition described above in an amount and duration effective to reduce inflammation in the brain and/or spinal cord of the subject. The pharmaceutical composition may be administered with a dosage of about 0.03 g/kg/day to about 0.3 g/kg/day of omega-3 essential fatty acid. The pharmaceutical composition may be administered within about 60 minutes to about 120 minutes of the trauma or injury.

In some embodiments, the pharmaceutical composition is initially administered with a dosage of about 0.2 g to about 5 g of the omega-3 essential fatty acids over 1-10 minutes. The pharmaceutical composition can be administered for a minimum of about 5 to about 21 days post-trauma or injury. In some embodiments, the subject is human. The methods of the invention can be used to treat a human suffering from traumatic brain injury which is mild, moderate or severe. When treating a spinal cord injury, the spinal cord injury can be incomplete. When treating stroke in a human, the stroke may be mild, moderate, or severe. The origin of the stroke may also be hemorrhagic or ischemic.

DESCRIPTION OF THE INVENTION

Intravenous Compositions

The present invention provides an intravenous pharmaceutical composition comprising at least one omega-3 essential fatty acid. The present invention also provides a method of modulating inflammatory response in a patient undergoing trauma, trauma brain injury, or and spine cord injury by intravenously administering a highly bioavailable, safe and stable pharmaceutical composition comprising at least one omega-3 essential fatty acid.

The term "omega-3 fatty acid" as used herein refers to a fatty acid in which a double bond is present at the third carbon from the methyl end of the hydrocarbon chain in the fatty acid.

The term "omega-6 fatty acid" as used herein refers to a fatty acid in which a double bond is present at the sixth carbon from the methyl end of the hydrocarbon chain in the fatty acid.

The term "omega-9 fatty acid" as used herein refers to a fatty acid in which a double bond is present at the ninth carbon from the methyl end of the hydrocarbon chain in the fatty acid The intravenous pharmaceutical compositions of the invention generally comprise, by way of example and not limitation, (a) an oil phase comprising at least one omega-3 essential fatty acid selected from a group consisting of α-linolenic acid (ALA), eicosapentaenoic acid (EPA), and docosahexaenoic acid (DHA), and at least one medium chain triglyceride (MCT), (b) at least one emulsifier, and (c) an aqueous phase, wherein the omega-3 essential fatty acid is in a concentration of about 50% to about 90% by weight of the oil phase.

By way of example, and not limitation, the intravenous pharmaceutical composition of the invention comprises EPA and DHA.

By way of example, and not limitation, the intravenous pharmaceutical composition of the invention comprises omega-3 essential fatty acid in a concentration range of about 50 g/L to about 300 g/L.

By way of example, and not limitation, the intravenous pharmaceutical composition of the invention comprises the medium chain triglycerides (MCTs). Medium-chain triglycerides are medium-chain (6 to 12 carbons) fatty acid esters of glycerol. Medium-chain triglycerides include but not limited to caproic acid, caprylic acid, capric acid and lauric acid. Preferably, Medium-chain triglycerides are caprylic acid and capric acid in a ratio range of about 3:2 by weight.

By way of example, and not limitation, the intravenous pharmaceutical composition of the invention comprises the oil phase and aqueous phase in a ratio of about 1:5 by volume. Preferably, the composition is a 20% oil-in-water emulsion.

By way of example, and not limitation, the intravenous pharmaceutical composition of the invention comprises an emulsifier. Preferably, the emulsifier is a natural biologically compatible emulsifier. The emulsifier can be a phospholipid compound or a mixture of phospholipids, such as lecithin, phosphatidylcholine, phosphatidyl ethanolamine or mixtures thereof. Non-limiting examples of phospholipids which can be used in the compositions of the invention are lecithins; Epikuron™ 170 being a mixture of about 70% (w/v) of phosphatidylcholine, 12% phosphatidylethanolamine, and about 16% other phospholipids, or Ovothin™ 160 being a mixture comprising about 60% (w/v) phosphatidylcholine, 18% (w/v) phosphatidylethanolamine, and 12% (w/v) other phospholipids, both manufactured by Lucas Meyer. These mixtures of mainly phosphatidylcholine and phosphatidylethanolamine are derived from a natural source, such as purified egg yolk phospholipids (for the Ovothin series) and soybean oil phospholipids (for the Epikuron series); a purified phospholipid mixture; Lipoid™ E-80 being a phospholipid mixture comprising about 80% (w/v) phosphatidylcholine, about 8% (w/v) phosphatidylethanolamine, about 3.6% non-polar lipids, and about 2% sphingomyeline, manufactured by Lipoid KG. Other phospholipids of plants (e.g., lecithin) or of animal origin known in the art can be used as emulsifiers for the preparations of the parenteral nutrition emulsion compositions of the invention. For example, other forms of emulsifiers containing fatty acyl groups, such as polyol fatty acid esters, can be used for the preparations of such emulsions.

Preferably, the amount of an emulsifier is from about 0.5 to about 4% (w/v). According to additional embodiments, the amount of the emulsifier is from about 0.5 to about 2.5% (w/v). According to an exemplary embodiment, the parenteral nutrition emulsion composition comprises about 1-1.2% (w/v) of the oil phase.

By way of example, and not limitation, the aqueous phase comprises an antioxidant agent. Antioxidants are commonly enzymes or other organic substances that are capable of counteracting the damaging effects of oxidation in the tissue. The antioxidant component of the composition according to the present invention may be selected from one or more of the group consisting of: allopurinol, carnosine, histidine, Coenzyme Q 10, n-acetyl-cysteine, superoxide dismutase (SOD), glutathione reductase (GR), glutathione peroxidase (GP) modulators and regulators, catalase and the other metalloenzymes, NADPH and AND(P)H oxidase inhibitors, glutathione, U-74006F, vitamin E, Trolox (soluble form of vitamin E), other tocopherols (gamma and alpha, beta, delta), tocotrienols, ascorbic acid, Vitamin C, Beta-Carotene (plant form of vitamin A), selenium, Gamma Linoleic Acid (GLA), alpha-lipoic acid, uric acid (urate), curcumin, bilirubin, proanthocyanidins, epigallocatechin gallate, Lutein, lycopene, bioflavonoids, polyphenols, Trolox®, dimethylthiourea, Tempol®, carotenoids, coenzyme Q, melatonin, flavonoids, polyphenols, aminoindoles, probucol and nitecapone, 21-aminosteroids or lazaroids, sulphydryl-containing compounds (thiazolidine, Ebselen, dithiolethiones), and N-acetylcysteine. Other antioxidants that could also be used include beta-mercaptopropionylglycine, O-phenanthroline, dithiocarbamate, selegilize and desferrioxamine (Desferal), an iron chelator, has been used in experimental infarction models, where it exerted some level of antioxidant protection. Spin trapping agents such as 5'-5-dimethyl-1-pyrrolione-N-oxide (DMPO) and (a-4-pyridyl-1-oxide)-N-t-butylnitrone (POBN) also act as antioxidants. Other antioxidants include: nitrone radical scavenger alpha-phenyl-tert-N-butyl nitrone (PBN) and derivatives PBN (including disulphur derivatives); N-2-mercaptopropionyl glycine (MPG) a specific scavenger of the OH free radical; lipooxygenase inhibitor nordihydroguaretic acid (NDGA); Alpha Lipoic Acid; Chondroitin Sulfate; L-Cysteine; oxypurinol and zinc.

By way of example, and not limitation, the emulsion composition further comprises an osmolality modifier such as glycerin, sorbitol, or alanine. The amount of an osmolality modifier can range from about 1 to about 5% (w/v).

By way of example, and not limitation, the emulsion composition further comprises other additives conventionally used in pharmaceutical compositions. Such additives include carbohydrate nutrients, electrolytes, amino acids, vitamins, trace minerals, preservatives, anti-foaming agents, buffering agents, chelating agents, tonicifiers and mixtures thereof. The amounts of such additives can be readily determined by one skilled in the art, according to the particular properties desired.

By way of example, and not limitation, the emulsion composition further comprises elevated divalent magnesium ions. Magnesium sulphate or magnesium chloride is a suitable source.

By way of example, and not limitation, the emulsion is isotonically adjusted to 280-500 mOsm per kg.

By way of example, and not limitation, pH of the emulsion for intravenous administration is adjusted to about 6 to about 8.5.

By way of example, and not limitation, omega-3 essential fatty acids in the pharmaceutical composition are small droplets in an emulsion. The United States Pharmacopeia (USP) Chapter 729 entitled "Globule Size Distribution in Lipid Injectable Emulsions" identifies two physical limits for emulsions: Method I: mean droplet size or MDS: <500 nm; Method II: percent of fat globules>5 micrometers or PFAT5: <0.05%. The present intravenous pharmaceutical composition meets the USP Chapter 729 emulsion requirements on globule size limits to ensure pharmaceutical equivalence and its safety profile in patients.

By way of example, and not limitation, the intravenous pharmaceutical composition can further comprise a pharmaceutically acceptable surfactant. Non-limiting examples of suitable anionic surfactants are the sodium, ammonium, and mono-, di-, and tri-ethanolamine salts of alkyl sulfates, alkyl ether sulfates, alkaryl sulfonates, alkyl succinates, alkyl sulfosuccinate, N-alkoyl sarcinates, alkyl phosphates, alkyl ether phosphates, alkyl ether carboxylates, and .alpha.-olefin sulfonates. The alkyl groups generally contain from 8 to 18 carbon atoms and may be unsaturated. The alkyl ether sulfates, alkyl ether phosphates, and alkyl ether carboxylates may contain from 1 to 10 ethylene oxide or propylene oxide units per molecule, and preferably contain 2 to 3 ethylene oxide units per molecule. Examples of the most preferred anionic surfactants include sodium or ammonium lauryl sulfate and sodium or ammoinium lauryl ether sulfate. Suitable nonionic surfactants include, but not limited to, aliphatic, primary or secondary linear or branched chain alcohols or phenols with alkylene oxides, generally ethylene oxide and generally 6-30 ethylene oxide groups. Other suitable nonionic surfactants include mono- or di-alkyl alkanolamides, alkyl polyglucosides, and polyhydroxy fatty acid amides. The amphoteric surfactants suitable for use in the present invention include alkyl amine oxides, alkyl betaines, alkyl amidopropyl betaines, alkyl sulfobetaines, alkyl glycinates, alkyl carboxyglycinates, alkyl amphopropionates, alkyl amidopropyl hydroxysultaines, acyl taurates, and acyl glutamates wherein the alkyl and acyl groups have from 8 to 18 carbon atoms. Nonlimiting examples of suitable cationic surfactants include water-soluble or water-dispersible or water-insoluble compounds containing at least one amine group which is preferably a quaternary amine group, and at least one hydrocarbon group which is preferably a long-chain hydrocarbon group. The hydrocarbon group may be hydroxylated and/or alkoxylated and may comprise ester- and/or amido- and/or aromatic-groups. The hydrocarbon group may be fully saturated or unsaturated.

By way of example, and not limitation, the intravenous pharmaceutical composition may comprise dramatically reduced amounts of omega-6 fatty acids, or eliminating omega-6 fatty acids altogether, and replacing the lipids with omega-3 fatty acids would provide prostaglandin precursors with less vasoactive series of eicosanoids and minimized inflammatory response.

In one embodiment, omega-6 fatty acid is absent from the emulsion. When omega-3 fatty acids are substituted for omega-6 fatty acids, omega-3 fatty acids such as EPA and DHA produce the more bioactive anti-inflammatory decosanoids and resolvins and less vasoactive, and relatively antiinflammatory 3-series of prostaglandins and thromboxanes along with the reduced immunomodulatory 5-series leukotrienes.

By way of example, and not limitation, the intravenous pharmaceutical composition comprises (a) about 5 to about 15 g/L of ALA and about 100 to about 125 g/L of EPA and DHA combined, (b) about 25 g/L of glycerol; (c) about 12 g/L of egg yolk phospholipids; and (d) about 100 mg/L of α-tocopherol.

Methods of Treatment

The present invention also provides a method of mitigating one or more symptoms associated with traumatic brain injury (TBI) and/or spinal cord injury (SCI) and/or stroke in a subject comprising intravenously administering a pharmaceutical composition comprising (a) an oil phase comprising (i) at least one omega-3 essential fatty acid selected from a group consisting of α-linolenic acid (ALA), eicosapentaenoic acid (EPA), and docosahexaenoic acid (DHA), and (ii) at least one medium chain triglyceride (MCT), (b) at least one emulsifier, and (c) an aqueous phase, wherein the omega-3 essential fatty acid is in a concentration of about 50% to about 90% by weight of the oil phase.

The present invention also provides a method of treating a subject following traumatic brain injury and/or spinal cord injury comprising intravenously administering a pharmaceutical composition comprising (a) an oil phase comprising (i) at least one omega-3 essential fatty acid selected from a group consisting of α-linolenic acid (ALA), eicosapentaenoic acid (EPA), and docosahexaenoic acid (DHA), and (ii) at least one medium chain triglyceride (MCT), (b) at least one emulsifier, and (c) an aqueous phase, wherein the omega-3 essential fatty acid is in a concentration of about 50% to about 90% by weight of the oil phase.

The present invention also provides a method of modulating an acute and/or sustained inflammatory response in a subject following traumatic brain injury and/or spinal cord injury comprising intravenously administering a pharmaceutical composition comprising (a) an oil phase comprising (i) at least one omega-3 essential fatty acid selected from a group consisting of α-linolenic acid (ALA), eicosapentaenoic acid (EPA), and docosahexaenoic acid (DHA), and (ii) at least one medium chain triglyceride (MCT), (b) at least one emulsifier, and (c) an aqueous phase, wherein the omega-3 essential fatty acid is in a concentration of about 50% to about 90% by weight of the oil phase.

The term "subject" refers to a mammal suffering from traumatic brain injury and/or spinal cord injury and/or stroke as defined herein and one or more symptoms associated herewith. The subject can be human and may be an adult, child or infant.

The term "treatment" or "treating" is used herein in the context of treating a condition, pertains generally to treatment and therapy, whether of a human or an animal (e.g., in veterinary applications), in which some desired therapeutic effect is achieved, for example, the inhibition of the progress of a symptom associated with TBI and/or SCI, and includes a reduction in the rate of progress, a halt in the rate of progress, amelioration of the symptom, and cure of the symptom.

By way of example, and not limitation, the intravenous pharmaceutical composition preferably comprises EPA and DHA or DHA alone. By way of example, and not limitation, the intravenous pharmaceutical composition comprises (a) about 5 to about 15 g/L of ALA and about 100 to about 125 g/L of EPA and DHA combined, (b) about 25 g/L of glycerol; (c) about 12 g/L of egg yolk phospholipids; and (d) about 100 mg/L of α-tocopherol. By way of example, and not limitation, the intravenous pharmaceutical composition is administered with a dosage of about 0.03 g/kg/day to about 0.3 g/kg/day of omega-3 essential fatty acid.

By way of example, and not limitation, the pharmaceutical composition is administered immediately after the trauma or injury event or within about 60 minutes to about 180 minutes of the trauma event.

By way of example, and not limitation, the pharmaceutical composition is initially administered with a dosage of about 2 g to about 5 g of the omega-3 essential fatty acids for a duration over 1-10 minutes. This followed by continuous intravenous administration to achieve a total daily dose of about 10 g to about 20 g per day for an adult for a minimum period of about 5 to about 21 days following the event.

The term "traumatic brain injury" (TBI) as used herein refers to physical damage to the brain resulting from external mechanical force, such as rapid acceleration or deceleration, impact, blast waves, or penetration by a projectile. Brain function is temporarily or permanently impaired and structural damage may or may not be detectable with current technology.

TBI is one of two subsets of acquired brain injury (brain damage that occurs after birth); the other subset is non-traumatic brain injury, which does not involve external mechanical force (examples include stroke and infection). All traumatic brain injuries are head injuries, but the latter term may also refer to injury to other parts of the head, including the spine. However, the terms head injury and brain injury can be used interchangeably. Similarly, brain injuries fall under the classification of central nervous system injuries and neurotrauma.

TBI is classified based on severity, anatomical features of the injury, and the mechanism (the causative forces). Mechanism-related classification divides TBI into closed and penetrating head injury. A closed (also called non-penetrating or blunt) injury occurs when the brain is not exposed. A penetrating, or open, head injury occurs when an object pierces the skull and breaches the dura mater, the outermost membrane surrounding the brain. The methods of the invention encompass treatment of all of the aforementioned TBI.

Traumatic brain injuries can be classified into mild, moderate, and severe categories. The Glasgow Coma Scale (GCS), the most commonly used system for classifying TBI severity, grades a person's level of consciousness on a scale of 3 to 15 based on verbal, motor, and eye-opening reactions to stimuli. It is generally agreed that a TBI with a GCS of 13 or above is mild, 9-12 is moderate, and 8 or below is severe. Similar systems exist in the pediatric setting. However, the GCS grading system has limited ability to predict outcomes. Another model developed by the Department of Defense and Department of Veterans Affairs uses all three criteria of GCS after resuscitation, duration of post-traumatic amnesia (PTA), and loss of consciousness (LOC). The use of neuroimaging to identify such symptoms as swelling, focal lesions, or diffuse injury is also widely employed. Grading scales also exist to classify the severity of mild TBI, commonly called concussion; these use duration of LOC, PTA, and other concussion symptoms. The methods of the invention encompass treatment of any of the aforementioned traumatic brain injury classifications with the intravenous compositions described herein.

The term "spinal cord injury" is used herein in the context of any injury to the spinal cord that is caused by trauma instead of a disease. Depending on where the spinal cord and nerve roots are damaged, the symptoms can vary widely, from pain to paralysis to incontinence. Spinal cord injuries are described at various levels of "incomplete" which can vary from having no effect on the patient to a "complete" injury which means a total loss of function. Spinal cord injuries have many causes, but are typically associated with major injuries from motor vehicle accidents, falls, sports injuries, and violence. It can also be involved in minor injuries, such as whiplash.

The American Spinal Injury Association (ASIA) defines an international classification based on neurological responses, touch and pinprick sensations tested in each dermatome, and strength of ten key muscles on each side of the body, including hip flexion (L2), shoulder shrug (C4), elbow flexion (C5), wrist extension (C6), elbow extension (C7). Traumatic spinal cord injury is classified into five categories by the American Spinal Injury Association and the International Spinal Cord Injury Classification System:
  A indicates a "complete" spinal cord injury where no motor or sensory function is preserved in the sacral segments S4-S5.
  B indicates an "incomplete" spinal cord injury where sensory but not motor function is preserved below the neurological level and includes the sacral segments S4-S5. This is typically a transient phase and if the person recovers any motor function below the neurological level, that person essentially becomes a motor incomplete, i.e. ASIA C or D.
  C indicates an "incomplete" spinal cord injury where motor function is preserved below the neurological level and more than half of key muscles below the neurological level have a muscle grade of less than 3, which indicates active movement with full range of motion against gravity.

D indicates an "incomplete" spinal cord injury where motor function is preserved below the neurological level and at least half of the key muscles below the neurological level have a muscle grade of 3 or more.

E indicates "normal" where motor and sensory scores are normal. Note that it is possible to have spinal cord injury and neurological deficits with completely normal motor and sensory scores.

The methods of the invention encompass treatment of any of the aforementioned classifications of SCI.

SCI symptoms experienced by a subject will vary depending on where the spine is injured and the extent of the injury. These are all determined by the area of the body that the injured area of the spine innervates. A section of skin innervated through a specific part of the spine is called a dermatome, and spinal injury can cause pain, numbness, or a loss of sensation in the relevant areas. A group of muscles innervated through a specific part of the spine is called a myotome, and injury to the spine can cause problems with voluntary motor control. The muscles may contract uncontrollably, become weak, or be completely unresponsive. The loss of muscle function can have additional effects if the muscle is not used, including atrophy of the muscle and bone degeneration. The methods of the invention encompass administration of the intravenous compositions described herein to alleviate or prevent one or more of the aforementioned symptoms, or any combination thereof, experienced by a subject with SCI.

A severe spinal cord injury may also cause problems in parts of the spine below the injured area. In a "complete" spinal injury, all functions below the injured area are lost. In an "incomplete" injury, some or all of the functions below the injured area may be unaffected. If the patient has the ability to contract the anal sphincter voluntarily or to feel a pinprick or touch around the anus, the injury is considered to be incomplete. The nerves in this area are connected to the very lowest region of the spine, the sacral region, and retaining sensation and function in these parts of the body indicates that the spinal cord is only partially damaged. The methods of the invention encompass treatment of a both complete and incomplete spinal cord injury so as to ameliorate the effects a subject would suffer from in the absence of treatment. The degree of amelioration may be partial or whole depending upon the extent of SCI. Generally, however, a higher degree of amelioration will be seen in less severe incomplete injuries when compared to severe complete injuries.

Stroke is one of two subsets of acquired brain injury that is non-traumatic; the other subset is traumatic brain injury. Stroke is the rapidly developing loss of brain function(s) due to disturbance in the blood supply to the brain. This can be due to ischemia (lack of blood flow) caused by blockage (thrombosis, arterial embolism), or a hemorrhage (leakage of blood).

The etiology of stroke is either ischemic, as in the majority of cases, or hemorrhagic. Ischemic stroke is usually caused by an embolus or a thrombus. The methods of the invention encompass treatment of either ischemic or hemorrhagic stroke via intravenous administration of an effective amount of any of the omega-3 fatty acid compositions described herein. After a massive cell death in the immediate core of the infarct caused by glucose and oxygen deficiency (cerebral ischemia), the zone of infarction grows for a few days due to secondary mechanisms such as glutamate excitotoxicity, inflammatory mechanisms, the production of free radicals and apoptotic mechanisms (Leker (2002) Brain Res. Rev. 39: 55-73). The methods of the invention encompass prevention and/or reduction of these secondary mechanisms to reduce the zone of infarction by intravenous administration of any of the omega-3 fatty acid compositions described herein. Assessment of the prevention or treatment methods described herein can be determined by the amount of reduction of the infarct volume of the subject suffering from a stroke. The infarct volume can be determined by magnetic resonance tomography; the DWI (diffusion-weighted image) method is used initially to determine the zone of previous cellular damage or destruction, whereas the PWI (perfusion-weighted image) method, which investigates the distribution of a contrast agent, provides information about the size of the tissue zone which is underperfused at the time. The tissue zone determined by PWI is often larger than that determined by DWI. In these cases, it is assumed that the effect of the treatment methods described herein can maintain the function of the part of the tissue zone determined by PWI which does not overlap with that determined by DWI, whereas it may be possible only less effectively to save the tissue area measured by DWI (Beaulieu (1999) Ann. Neurol. 46: 568-578; Wu (2001) Stroke 32: 933-942).

Rating scales such as the modified Rankin scale or the National Institute of Health stroke scale (NIHSS) are generally used for the quantitative evaluation of the severity of a stroke, whether acute or under treatment. While the Rankin scale permits very rough classification of a patient's neurological status (from the value "0" for free from symptoms to the value "6" for dead), the NIH stroke scale permits a high-resolution evaluation of a patient's neurological status. To obtain the finding on the NIH stroke scale, various neurological aspects are investigated and assigned point scores. The total point score is a measure of the severity of the symptoms of stroke, the point score increasing with the severity of the symptoms. These rating scales are also suitable for monitoring the course of the symptoms after stroke and for quantifying the success of any treatment used. In general, it is possible to establish a correlation between the size of the infarct and the severity of the stroke as quantified by the stroke scale (Beaulieu (1999) Ann. Neural. 46: 568-578). Hence, the course of the size of the infarct under treatment is also suitable for the assessment of a treatment effect. The methods of the invention encompass treatment of stroke with the intravenous omega-3 fatty acids described herein in an amount effective and duration sufficient to alleviate the symptoms of stroke in the patient. In some embodiments, the amount and duration are described herein and are sufficient to change the point score of the patient as assessed by the Rankin or NIHSS. In some embodiments, the amount and duration of treatment is sufficient to decrease the Rankin point value from 5 to 4, 4 to 3, 3 to 2 or 2 to 1, or a decrease in value in any range in between these values.

EXAMPLES

Without further description, it is believed that one of ordinary skill in the art can, using the preceding description and the following illustrative examples, make and utilize the present invention and practice the claimed methods. The following working examples, therefore, specifically point out representative embodiments of the present invention, some preferred, and are not to be construed as limiting in any way the remainder of the disclosure.

Materials and Methods

MCT solution was purchased from Croda (Singapore). The MCT solution contained 58% Caprylic acid and 42% Capric acid. According to the manufacturer, both fatty acids are distributed randomly on the glycerol backbone. DHA and EPA were obtained from K. D. Pharma, Germany. Arachidonic acid bound to glycerol in a form of triglycerides was obtained from Martek, USA, at a concentration of 20%. All solvents and chemicals were obtained from Sigma and were of analytical grade.

Example 1

Clinical experience treating a variety of patients with high dose oral omega-3 fatty acids supplements following TBI. In a half dozen mild TBI cases including one refractory TBI case from Operation Iraqi Freedom, patients universally reported noticing a significant improvement in headaches and focus within two days after beginning a dose of nine grams a day. Additional comments in those patients and several others have included feeling a sense of calmness and less agitation. One patient with a significant history of depression and suicidal ideation reported by the end of day one of treatment, a profound sense of "happiness" that he had not experienced since ceasing his antidepressant medications six months prior to the treatment. In one case of moderate TBI with documented CT and MRI abnormalities, the patient reported a decrease of his double vision within two days while continuing to improve on a high dose oral regimen. In one case of severe TBI, the surviving driver was placed on enteral feeds of omega-3 fatty acids supplementation. Starting post-injury day ten with a cautious dose, within two days, the comatose patient began to have small eye and hand movements in response to verbal stimuli. The amount of omega-3 fatty acids was then gradually increased. Within three months, the patient was discharged from inpatient rehabilitation care and stood on the stage to receive his high school diploma.

Example 2

An intravenous pharmaceutical composition of the invention to be administered in patients suffering from TBI or spinal cord injury (SCI) will be via an intravenous route through a dedicated port on a central venous line. The intravenous pharmaceutical composition comprises total omega-3 fatty acids dose of about 0.03 to about 0.3 g/kg/day.

Within 60-120 minutes of a trauma injury event, the composition is administered intravenously for a period of about 1-10 min. Preferably, a total amount of about 2 g to 5 g omega-3 fatty acids is intravenously administered within 60-120 minutes of the trauma event. This is followed by continuous intravenous administration for a minimum period of 5-21 days following the injury event.

For a 70 kg subject with the dose of 0.3 g/kg/day: 0.3×70=21 g omega-3 fatty acids continuously administered per day a rate of 14.6 mg/min. If constantly infused for 1 hour on a 70 kg subject: total amount of omega-3 fatty acids administered if constantly infused for 60 min equates to 60×14.6=876 mg omega-3 fatty acids.

For a 70 kg subject with the dose of 0.03 g/kg/day: 0.03×70=2.1 g omega-3 fatty acids continuously administered per day a rate of 1.46 mg/min. If constantly infused for 1 hour on a 70 kg subject: total amount of omega-3 fatty acids administered if constantly infused for 60 min equates to 60×1.46=87.6 mg omega-3 fatty acids.

For a 5 kg infant with the dose of 0.3 g/kg/day: 0.3×5=1.5 g omega-3 fatty acids continuously administered per day a rate of 1.04 mg/min. If constantly infused for 1 hour on a 5 kg subject: total amount of omega-3 fatty acids administered if constantly infused for 60 min equates to 60×1.04=6.2 mg omega-3 fatty acids.

For a 5 kg infant with the dose of 0.03 g/kg/day: 0.3×5=0.15 g omega-3 fatty acids continuously administered per day a rate of 0.104 mg/min. If constantly infused for 1 hour on a 5 kg subject: total amount of omega-3 fatty acids administered if constantly infused for 60 min equates to 60×0.104=0.62 mg omega-3 fatty acids.

After administration for 5-7 days, subjects are provided with oral or enteral supplementation of omega-3 fatty acids for several months forward.

Example 3

1 L "OmegaPlus" 200 mg/ml Composition a. 5 to 15 g/L of ALA, and 100 to 125 g/L of EPA & DHA combined,
b. 25 g/L of glycerol;
c. 12 g/L of egg yolk phospholipids; and
d. 100 mg/L of α-tocopherol.

While the invention has been described and illustrated herein by references to various specific materials, procedures and examples, it is understood that the invention is not restricted to the particular combinations of material and procedures selected for that purpose. Numerous variations of such details can be implied as will be appreciated by those skilled in the art. It is intended that the specification and examples be considered as exemplary, only, with the true scope and spirit of the invention being indicated by the following claims. All references, patents, and patent applications referred to in this application are herein incorporated by reference in their entireties.

The invention claimed is:

1. A method of treating a subject suffering from traumatic brain injury, spinal cord injury and/or stroke comprising intravenously administering a pharmaceutical composition in an amount effective to reduce inflammation in the brain and/or spinal cord of the subject, wherein the pharmaceutical composition is a stable intravenous pharmaceutical composition comprising:
   a. an oil phase comprising
      i. omega-3 essential fatty acids comprising about 5 to about 15 g/L α-linolenic acid (ALA); and about 100 to about 125 g/L of eicosapentaenoic acid (EPA) and docosahexaenoic acid (DHA) combined, and
      ii. at least one medium chain triglyceride (MCT),
   b. about 12 g/L of egg yolk phospholipids as an emulsifier, and
   c. an aqueous phase comprising about 25 g/L of glycerol and about 100 mg/L of α-tocopherol, wherein the oil and aqueous phase form a 20% oil in water emulsion, and
   wherein the omega-3 essential fatty acid is in a concentration of about 50% to about 90% by weight of the oil phase, and wherein omega-6 fatty acids are absent.

2. The method according to claim 1, wherein the pharmaceutical composition is administered with a dosage of about 0.03 g/kg/day to about 0.3 g/kg/day of omega-3 essential fatty acids.

3. The method according to claim 1, wherein the pharmaceutical composition is administered within about 60 minutes to about 120 minutes of the trauma or injury.

4. The method according to claim 2, wherein the pharmaceutical composition is initially administered with a dosage of about 0.2 g to about 5 g of the omega-3 essential fatty acids over 1-10 minutes.

5. The method according to claim 1, wherein the pharmaceutical composition is administered for a minimum of about 5 to about 21 days post trauma or injury.

6. The method according to claim 1, wherein the subject is human.

7. The method according to claim 6, wherein the traumatic brain injury is mild, moderate or severe.

8. The method according to claim 6, wherein the spinal cord injury is incomplete.

9. The method according to claim 6, wherein the stroke is mild, moderate, or severe.

10. The method according to claim 6, wherein the stroke is hemorrhagic or ischemic.

11. The method according to claim 1, wherein the omega-3 fatty acids is in a concentration range of about 105 g/L to about 300 g/L.

12. The method according to claim 1, wherein the at least one medium chain triglyceride are caprylic acid and capric acid.

13. The method according to claim 12, wherein the caprylic acid and capric acid are in a ratio range of about 3:2 by weight.

14. A method of treating an adult subject suffering from traumatic brain injury, spinal cord injury and/or stroke comprising intravenously administering a pharmaceutical composition comprising:
 a. an oil phase comprising
  i. at least one omega-3 essential fatty acid selected from a group consisting of α-linolenic acid (ALA), eicosapentaenoic acid (EPA), and docosahexaenoic acid (DHA), and
  ii. at least one medium chain triglyceride (MCT),
 b. at least one emulsifier in a concentration of 0.5% to 4%, and
 c. an aqueous phase, wherein the oil and aqueous phase form a 20% oil in water emulsion, and
 wherein the omega-3 essential fatty acid is in a concentration of about 50% to about 90% by weight of the oil phase, and wherein omega-6 fatty acids are absent; and
 wherein the composition is initially administered with a dosage of about 2 g to about 5 g of the at least one omega-3 essential fatty acid for a duration of 1-10 minutes, followed by continuous administration to a total dose of about 10 g to about 20 g per day.

* * * * *